United States Patent
Billodeaux et al.

(10) Patent No.: US 9,227,903 B2
(45) Date of Patent: Jan. 5, 2016

(54) REDUCTION OF ESTER FORMATION IN ISOBUTYRALDEHYDE OXIDATION

(71) Applicant: Eastman Chemical Company, Kingsport, TN (US)

(72) Inventors: Damon Ray Billodeaux, Longview, TX (US); Kenneth Wayne Hampton, Jr., Gilmer, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/105,945

(22) Filed: Dec. 13, 2013

(65) Prior Publication Data
US 2015/0166450 A1 Jun. 18, 2015

(51) Int. Cl.
*C07C 51/34* (2006.01)
*C07C 51/347* (2006.01)
*C07C 51/235* (2006.01)

(52) U.S. Cl.
CPC .................................. *C07C 51/235* (2013.01)

(58) Field of Classification Search
CPC ............................. C07C 51/34; C07C 51/347
USPC .......................................... 562/523, 531, 532
See application file for complete search history.

(56) References Cited

U.S. PATENT DOCUMENTS 4,350,829 A 9/1982 Masuko et al.
2006/0052633 A1* 3/2006 Lee et al.

FOREIGN PATENT DOCUMENTS

EP 0 855 996 B1 1/2002
WO WO 98/25876 A1 6/1998

OTHER PUBLICATIONS

Lehtinen, Christel et al.; "Experimental and computational studies on solvent effects in reactions of peracid-aldehyde adducts"; Tetrahedron; Mar. 2001; vol. 57, pp. 4741-4751.
Notification of Transmittal of the International Search Report and the Written Opinion of the International Searching Authority, or the Declaration date of mailing Mar. 4, 2015 received in International Patent Application No. PCT/US2014/070047.

* cited by examiner

Primary Examiner — Kamal Saeed
Assistant Examiner — Janet L Coppins
(74) Attorney, Agent, or Firm — James Arnold, Jr.

(57) ABSTRACT

The oxidation of isobutyraldehyde produces isobutyric acid and byproducts, such as isopropyl formate. A method of reducing the isopropyl formate byproduct in the oxidation of isobutyraldehyde is described. The method uses a co-solvent, such as acetone, to the isobutyraldehyde feed to increase both the selectivity of the reaction to isobutyric acid and the production rate of isobutyric acid so that the isopropyl formate byproduct is significantly reduced.

23 Claims, No Drawings

REDUCTION OF ESTER FORMATION IN ISOBUTYRALDEHYDE OXIDATION

BACKGROUND OF THE INVENTION

Production of isobutyric acid (iHOBu) is accomplished by the catalyzed or uncatalyzed oxidation of isobutyraldehyde (iHBu). FIG. 1 illustrates that the oxidation of the aldehyde results in the formation, first of peroxyacid, followed by the generation of an intermediate that can lead to production of two moles of the desired acid (Pathway A), with an undesired by-product, isopropyl formate (IPF), produced by the Bayer-Villager oxidation of isobutyraldehyde (Pathway B).

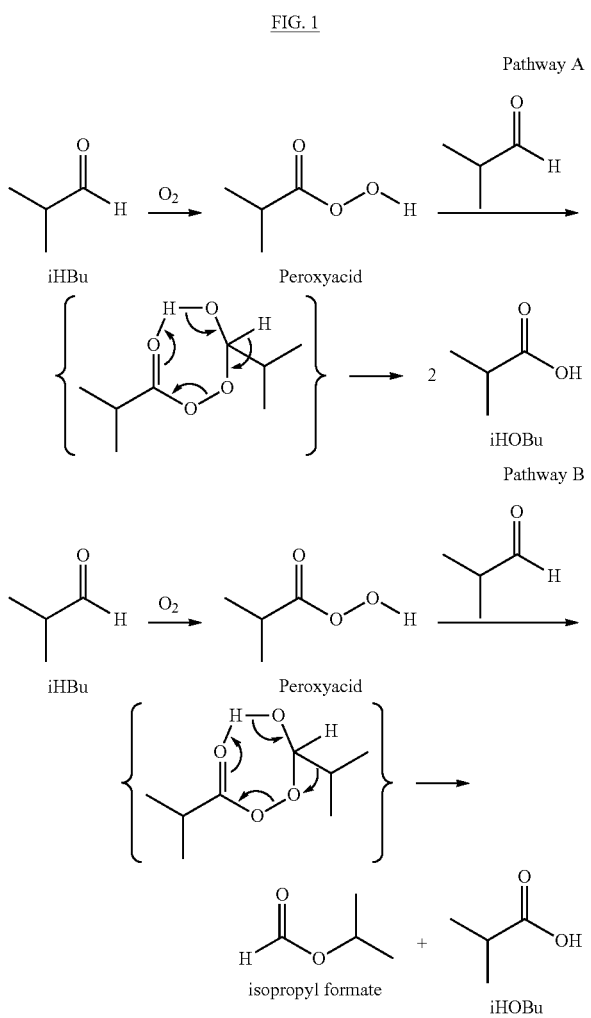

FIG. 1

As seen in FIG. 1, iHBu can form either the desired acid or the undesired byproduct IPF. In Pathway A, the movement of electrons from a C—H bond on the peroxy acid-aldehyde intermediate results in the formation of two moles of the desired carboxylic acid product. In Pathway B, the electrons move from a C—C bond on the intermediate to form one mole of iHOBu and one mole of the undesired IPF byproduct. Low selectivity for Pathway A results in the loss of some of the iHBu feed to form of the undesired byproduct IPF. In view of problems associated with low selectivity of iHBu oxidation, it would be beneficial if Pathway B of the oxidation mechanism could be impeded so that less byproduct IPF will be produced and more desired acid will be produced.

IPF not only consumes valuable raw materials and lowers the production of the desired acid, it also has other drawbacks. For example, IPF byproduct is very difficult to be separated from unreacted starting materials. The separation of IPF from the reaction mixture is usually accompanied by unreacted isobutyraldehyde (iHBu) due to the proximity of their boiling points. Accordingly, the formation of IPF by-product is a significant financial burden on commercial production of isobutyric acid.

BRIEF SUMMARY OF THE INVENTION

According to an embodiment, the present invention provides a method for reducing the byproduct of isopropyl formate in a process of producing isobutyric acid comprising contacting isobutyraldehyde and a co-solvent, such as acetone, in the presence of an oxidant to form isobutyric acid, wherein the formation of isopropyl formate by-product is significantly reduced comparing with the same process without using the co-solvent. When the co-solvent is acetone, the acetone can be collected from the system, self-satisfied as is in the system or freshly added to the system, or any combination thereof.

DETAILED DESCRIPTION

According to an embodiment, the invention concerns a method for increasing the production of isobutyric acid by reducing the formation of IPF by-product in the oxidation of isobutyraldehyde by using a co-solvent. Preferably, the co-solvent is acetone. According to an embodiment, the invention concerns the finding that the use of acetone as a co-solvent with a solvent, wherein the solvent is, for example, isobutyric acid, water, or a saturated hydrocarbon, such as hexane, pentane, heptane, octane, etc. in the oxidation of isobutyraldehyde to increase the selectivity and yield of isobutyric acid. Usually, adding co-solvent to a feed in a process will decrease the yield of the final product. Surprisingly, it has been found that despite a decrease in concentration of isobutyraldehyde feed, the overall production rate of isobutyric acid is almost the same or even higher comparing to the process in which no co-solvent is used.

According to an embodiment, the invention concerns a method for producing isobutyric acid comprising contacting isobutyraldehyde, a solvent and an acetone co-solvent in the presence of an oxidant to form isobutyric acid, wherein the amount of IPF by-product is reduced comparing with the same process wherein no acetone co-solvent is used. Surprisingly, the amount of isopropyl formate by product is reduced by about 30% to about 40% by weight, by about 40% to about 60% by weight, by about 60% to about 80% by weight, or even by about 80% to about 95.5% by weight. According to another embodiment, the co-solvent may also be ethyl acetate.

Acetone is used as a co-solvent to increase the selectivity of production of isobutyric acid from oxidation of isobutyraldehyde. The co-solvent may be present in any percentage from about 1 to about 51 weight % by total weight of reaction solution, from about 5 to about 50 weight % by total weight of reaction solution, or even from about 10 to about 25 weight % by total weight of reaction solution.

In many isobutyric acid processes, acetone is formed as a byproduct of isobutyraldehyde oxidation. This acetone can be collected from the process. Optionally the collected acetone can be further concentrated through normal means—particularly distillation. The collected acetone can be reused as co-feed with isobutyraldehyde such that the isobutyraldehyde/ acetone mixtures listed above are utilized. It is advantageous to use the acetone by-product from the process because
  i) Collected acetone eliminates the cost of purchasing fresh acetone;
  ii) acetone is not foreign to the operating system/process/method;
  iii) the separated byproduct acetone does not have to be disposed thus saving disposal costs and reducing environmental impact due to incineration of hazardous waste handling; and Alternatively, effective use of distillation and decantation can allow the acetone to build up in the system to a level that will self-satisfy the process of the invention. Therefore, no need to add additional acetone to the process. Optional, minor amount of acetone can be added.

According to an embodiment, the method of producing isobutyric acid involving the oxidation (such as liquid phase oxidation) of isobutyraldehyde, can be carried out in the presence or absence of a catalyst. Optionally, acceptable catalysts such as, noble metal or transition metal salts can be used. Salts of Co, Cr, or Mn are also useful for catalyzed oxidation of isobutyric acid. In many cases, uncatalyzed oxidation of isobutyric acid is just as or more effective than catalyzed oxidation.

The method can be carried out at a range of temperatures. Typically, oxidation of isobutyraldehyde is carried out from about 0° C. to about 100° C., from about 25° C. to about 50° C., or even from about 35° C. to about 45° C.

The method may be run at about ambient pressure to about 200 psig, from about 20 psig to about 60 psig, or event from about 40 psig to about 55 psig.

The method may be carried out in any type of reactor familiar to those skilled in the art. The reaction can be carried out in a batch reactor such as an autoclave or stirred reactor. It can also be carried out in a continuous method using a plug flow reactor, bubble column, or heated tube type reactor.

Any known oxidant can be used to effect the transformation of isobutyraldehyde to isobutyric acid. Examples of such oxidants include gas mixtures containing oxygen (e.g. air). Pure oxygen may also be used. Liquid oxidants such as solutions of sodium hypochlorite and hydrogen peroxide can also be used.

The target product, isobutyric acid, can be recovered from the reaction mixture by any known means. For example, the reaction product of the uncatalyzed reaction may be run through a series of distillation columns such that acetone and unreacted isobutyraldehyde are recovered and recycled to the reactor. Non-selective products, such as isopropyl formate, are separated, and purified isobutyric acid is recovered. Decantation, evaporation, liquid-liquid extraction, or gas stripping can also be used to purify the isobutyric acid product and/or recover the acetone solvent.

The catalyzed process may likewise be run through a series of distillation columns such that acetone and unreacted isobutyraldehyde are recovered and recycled, isobutyric acid is recovered and purified, and the concentrated catalysts solution removed as a base heel and recycled to the reactor. The catalyst may also be recovered by gas stripping the reactor solution to recover organics, water, and acids prior to distillation thus leaving a catalyst rich solution to be recycled to the reactor. Decantation, evaporation, or liquid-liquid extraction may also be useful for separation of reaction products and recovery of the catalyst solution.

EXAMPLES

This invention can be further illustrated by the following examples of preferred embodiments thereof, although it will be understood that these examples are included merely for purposes of illustration and are not intended to limit the scope of the invention unless otherwise specifically indicated.

The examples given were all carried out in a laboratory scale continuous oxidation reactor. The reactor was constructed of an 18"×1.5" 316 stainless steel pipe. The bottom of the pipe was capped with a ¼" O.D. stainless steel tube, topped on one end with a 15 micron frit, run through the cap. Liquids were pumped into the column via a laboratory scale pump capable of feed rates up to 20 mL/min and pressures up to 3000 psig. Air was supplied from a compressed gas cylinder and its flow rate controlled by means of a standard rotometer. The liquid and gas feed lines were joined at a "tee" before passing through the frit into the reactor. Pressure in the reactor was controlled by means of back pressure regulator.

The reactor was wrapped in electrically heated tape and controlled by an electronic heater which monitors the skin temperature of the reactor via a J-type thermocouple. A "cold finger" comprised of a ½" O.D. stainless steel tube sealed at one end and filled with chilled glycol, ran from the top of the reactor to ¾ of the length of the pipe in the reaction mixture and was used to remove generated heat and control the internal temperature. The internal temperature was monitored by an internal K-type thermocouple connected to an electronic controller. The controller operated a solenoid valve which allowed glycol into the "finger" when the internal temperature exceeded a set point.

The top of the reactor is fitted with two "pipe tees" that allow for liquid and gas overflow. The liquid overflow passed through the first tee into a glycol chilled condenser and into a product tank. The gas overflow passed through the second tee, through the back pressure regulator. The gas overflow passed through three dry ice traps to collect more condensables. The liquid from these dry ice traps was combined with the liquid overflow and analyzed by gas chromatogram. The gas from the third ice trap was periodically sampled and analyzed by GC as well.

In a typical experiment, the reactor was filled with isobutyric acid and the appropriate weight % of acetone. The reactor was heated to an internal temperature of 40° C. under 55 psig. Upon reaching the desired internal temperature, a feed tank is charged with isobutyraldehyde and the desired weight % of acetone. The mixture is fed into the reactor at a rate of 1.5 mL/min. Air is fed into the reactor at a rate of 1 SLPM. The internal temperature is monitored and maintained at 40° C. The pressure is maintained at 55 psig. The liquid overflow is measured and weighed every hour and a sample analyzed by GC. The gas outlet is sampled and analyzed by GC periodically. A typical experiment lasts 7 hours.

For the purposes of this invention and the following examples, selectivity is defined by the following equation:

$$\% \text{ Selectivity} = \text{Mols of isobutyric acid produced} \times 100\% \text{ Mols of isobutyraldehyde converted}$$

Example 1

Control, Oxidation of iHBu with 0% Acetone

The reactor is charged with 540 mL of isobutyric acid. After heating to 40° C. under 55 psig, iHBu is fed into the reactor at 1.5 mL/min. Air is fed into the reactor at 1 SLPM. Liquid overflow and gas effluent is collected, weighed, and analyzed by GC hourly. After 7 hours, the feeds are ceased, gas is vented, and the reactor is cooled, emptied, and its contents weighed and analyzed. The overflow was found to contain 91.0% isobutyric acid, 3.96% IPF, 2.48% acetone, 1.48% iHBu, 0.97% $CO_2$ and 0.11% isopropanol.

Example 2

Oxidation of iHBu with 5% Acetone

The reactor is charged with 540 mL of 95% isobutyric acid and 5% acetone. After heating to 40° C. under 55 psig, a mixture of 95% iHBu and 5% acetone is fed into the reactor at 1.5 mL/min. Air is fed into the reactor at 1 SLPM. Liquid overflow and gas effluent is collected, weighed, and analyzed by GC hourly. After 7 hours, the feeds are ceased, gas is vented, and the reactor is cooled, emptied, and its contents weighed and analyzed. The overflow was found to contain 86.0% isobutyric acid, 2.25% IPF, 8.72% acetone, 2.45% iHBu, 0.55% $CO_2$, and 0.0% isopropanol.

Example 3

Oxidation of iHBu with 10% Acetone

The reactor is charged with 540 mL of 90% isobutyric acid and 10% acetone. After heating to 40° C. under 55 psig, a mixture of 90% iHBu and 10% acetone is fed into the reactor at 1.5 mL/min. Air is fed into the reactor at 1 SLPM. Liquid overflow and gas effluent is collected, weighed, and analyzed by GC hourly. After 7 hours, the feeds are ceased, gas is vented, and the reactor is cooled, emptied, and its contents weighed and analyzed. The overflow was found to contain 79.5% isobutyric acid, 2.28% IPF, 14.71% acetone, 2.98% iHBu, 0.53% $CO_2$, and 0.0% isopropanol.

Example 4

Oxidation of iHBu with 25% Acetone

The reactor is charged with 540 mL of 75% isobutyric acid and 25% acetone. After heating to 40° C. under 55 psig, a mixture of 75% iHBu and 25% acetone is fed into the reactor at 1.5 mL/min. Air is fed into the reactor at 1 SLPM. Liquid overflow and gas effluent is collected, weighed, and analyzed by GC hourly. After 7 hours, the feeds are ceased, gas is vented, and the reactor is cooled, emptied, and its contents weighed and analyzed. The overflow was found to contain 72.7% isobutyric acid, 1.34% IPF, 23.5% acetone, 2.10% iHBu, 0.37% $CO_2$, and 0.02% isopropanol.

Example 5

Oxidation of iHBu with 50% Acetone

The reactor is charged with 540 mL of 50% isobutyric acid and 50% acetone. After heating to 40° C. under 55 psig, a mixture of 50% iHBu and 50% acetone is fed into the reactor at 1.5 mL/min. Air is fed into the reactor at 1 SLPM. Liquid overflow and gas effluent is collected, weighed, and analyzed by GC hourly. After 7 hours, the feeds are ceased, gas is vented, and the reactor is cooled, emptied, and its contents weighed and analyzed. The overflow was found to contain 53.4% isobutyric acid, 0.19% IPF, 45.8% acetone, 0.49% iHBu, 0.22% $CO_2$, and 0.00% isopropanol.

TABLE 1

| Ex | Acetone | iHBu Conversion | iHOBu Selectivity | iHOBu Yield | iHOBu Production (g/h) | IPF | Reduced IPF |
|---|---|---|---|---|---|---|---|
| 1 | 0% | 96.2% | 82.4% | 81.1% | 47.1 | 3.96% | 0% |
| 2 | 5% | 96.1% | 85.4% | 85.4% | 44.2 | 2.25% | 43% |
| 3 | 10% | 92.5% | 85.5% | 85.5% | 44.9 | 2.28% | 42% |
| 4 | 25% | 94.2% | 86.0% | 81.1% | 50.0 | 1.34% | 66% |
| 5 | 50% | 96.5% | 89.9% | 89.9% | 27.3 | 0.19% | 95.3% |

Table 1 shows the increase in selectivity and yield of isobutyric acid as the weight % of acetone co-solvent is increased from 0% to 50%. At 50%, the production rate of mass of acid per hour falls to levels that counteract the benefits of increased yield.

Example 6

Oxidation of 2-ethylhexanal

The oxidation reactor described above is charged with 500 mL of 2-ethylhexanoic acid. The reactor is heated to 40° C. under 5 psi of air (typical conditions for a commercial 2-ethylhexanoic acid reactor). 2-ethylhexanal is fed at 1.0 mL/min and purified air at 1000 SCCM. The reactor effluent is collected, weighed, and analyzed each hour. The overflow is comprised of 85.9% acid, 7.94% 2-ethylhexanal, 4.27% heptyl formate (HPF), 0.83% 3-heptanone, 0.94% 3-heptanol, 0.12% heptane, and 0% acetone.

Example 7

Oxidation of 2-ethylhexanal with 10% acetone

The oxidation reactor described above is charged with 500 mL of 90% 2-ethylhexanoic acid and 10% acetone. The reactor is heated to 40° C. under 5 psi of air (typical conditions for a commercial 2-ethylhexanoic acid reactor). A mixture of 90% 2-ethylhexanal and 10% acetone is fed at 1.0 mL/min and purified air at 1000 SCCM. The reactor effluent is collected, weighed, and analyzed each hour. The overflow is comprised of 73.1% acid, 5.59% 2-ethylhexanal, 10.8% heptyl formate, 1.20% 3-heptanone, 0.72% 3-heptanol, 0.18% heptane, and 8.41% acetone.

Example 8

Oxidation of 2-ethylhexanal with 25% acetone

The oxidation reactor described above is charged with 500 mL of 75% 2-ethylhexanoic acid and 25% acetone. The reactor is heated to 40° C. under 5 psi of air (typical conditions for a commercial 2-ethylhexanoic acid reactor). A mixture of 75% 2-ethylhexanal and 25% acetone is fed at 1.0 mL/min and purified air at 1000 SCCM. The reactor effluent is collected, weighed, and analyzed each hour. The overflow is comprised of 58.2% acid, 2.52% 2-ethylhexanal, 14.1% heptyl formate, 1.80% 3-heptanone, 0.80% 3-heptanol, 0.22% heptane, and 22.3% acetone.

TABLE 2

| Example | % Acetone | 2-ethylhexanal Conversion | 2-ethylhexanoic Acid Selectivity | % HPF |
|---|---|---|---|---|
| 6 | 0% | 92.0% | 88.7% | 4.27% |
| 7 | 10% | 93.2% | 75.1% | 10.8% |
| 8 | 25% | 96.9% | 64.6% | 14.1% |

Examples 6-8 are summarized in Table 2. Table 2 indicates that the use of acetone as a co-solvent cannot reduce the HPF byproduct in a similar process of making 2-ethylhexanoic acid. In fact, it increased the HPF byproduct by more than 100%. As the concentration of acetone increases in the feed, the selectivity to 2-ethylhexanoic acid decreases and the concentration of heptyl formate increases.

Example 9

Oxidation of isobutyraldehyde with 10% ethyl acetate

The oxidation reactor described above is charged with 540 mL of 90% isobutyric acid and 10% ethyl acetate. The reactor is heated to 40° C. under 55 psig of air. A mixture of 90% isobutyraldehyde and 10% ethyl acetate is fed at 1.0 mL/min and purified air at 1000 SCCM. The reactor effluent is collected, weighed, and analyzed each hour. The overflow is comprised of 89.8% isobutyric acid, 6.66% ethyl acetate, 1.81% isopropyl formate, 0.88% acetone, 0.80% iHBu, 0.04% $CO_2$.

Example 10

Oxidation of isobutyraldehyde with 25% ethyl acetate

The oxidation reactor described above is charged with 540 mL of 75% isobutyric acid and 25% ethyl acetate. The reactor is heated to 40° C. under 55 psig of air. A mixture of 75% isobutyraldehyde and 25% ethyl acetate is fed at 1.0 mL/min and purified air at 1000 SCCM. The reactor effluent is collected, weighed, and analyzed each hour. The overflow is comprised of 78.7% isobutyric acid, 17.2% ethyl acetate, 2.12% isopropyl formate, 0.30% acetone, 1.67% iHBu, 0.04% $CO_2$.

TABLE 3

| Example | % ethyl acetate | iHBu Conversion | iHOBu Selectivity | iHOBu Yield | % IPF |
|---|---|---|---|---|---|
| 1 | 0% | 96.2% | 82.4% | 81.1% | 3.96% |
| 9 | 10% | 97.5% | 84.6% | 82.3% | 1.81% |
| 10 | 25% | 95.6% | 83.9% | 78.8% | 2.12% |

The results in Table 3 show that the use of ethyl acetate as the co-solvent can also reduce the IPF byproduct. However, the effect of ethyl acetate is not as good as acetone.

The invention has been described in detail with particular reference to preferred embodiments thereof, but it will be understood that variations and modifications can be effected within the spirit and scope of the invention.

The invention claimed is:

1. A method for reducing isopropyl formate in a process of producing isobutyric acid comprising contacting isobutyraldehyde, a solvent and acetone in the presence of an oxidant to form isobutyric acid, wherein the formation of isopropyl formate is reduced comparing with the production of isobutyric acid in the absence of acetone, wherein the acetone is present in an amount of from about 10 to about 25 weight % by total weight of reaction solution, and wherein at least some of the acetone is a byproduct collected from the process.

2. The method of claim 1, wherein the acetone is byproduct collected from the process and no fresh acetone is added.

3. The method of claim 2 wherein the solvent is isobutyric acid.

4. The method of claim 2 wherein the solvent is isobutyric acid, water, or a saturated hydrocarbon.

5. The method of claim 2, wherein the formation of the isopropyl formate is reduced by about 30% to about 95.5% by weight.

6. The method of claim 2, wherein the formation of the isopropyl formate is reduced by about 40% to about 80% by weight.

7. The method of claim 2, wherein the formation of the isopropyl formate is reduced by about 40% to about 60% by weight.

8. The method of claim 1 wherein at least some fresh acetone is added to the process.

9. The method of claim 8 wherein the solvent is isobutyric acid.

10. The method of claim 8 wherein the solvent is isobutyric acid, water, or a saturated hydrocarbon.

11. The method of claim 8, wherein the formation of the isopropyl formate is reduced by about 30% to about 95.5% by weight.

12. The method of claim 8, wherein the formation of the isopropyl formate is reduced by about 40% to about 80% by weight.

13. The method of claim 8, wherein the formation of the isopropyl formate is reduced by about 40% to about 60% by weight.

14. The method of claim 1, wherein the method is carried out at a temperature of 0 to 100° C.

15. The method of claim 1, wherein the method is carried out at a temperature of 25 to 50° C.

16. The method of claim 1, wherein the method is carried out at a temperature of 35 to 45° C.

17. The method of claim 1, wherein the method is carried out at a pressure of 20 to 50 psig.

18. The method of claim 1, wherein the method is carried out at a pressure of 40 to 55 psig.

19. The method of claim 1, wherein contacting the isobutyraldehyde, the solvent and the acetone occurs in the presence of an oxidation catalyst.

20. The method of claim 19, wherein the catalyst is selected from a noble metal, transition metal salts, and Salts of Co, Cr, or Mn.

21. The method of claim 1, further comprising concentrating acetone that is a byproduct of the process and co-feeding it to the process with the isobutyraldehyde.

22. The method of claim 2, further comprising concentrating acetone that is a byproduct of the process and co-feeding it to the process with the isobutyraldehyde.

23. The method of claim 8, further comprising concentrating acetone that is a byproduct of the process and co-feeding it to the process with the isobutyraldehyde.

* * * * *